United States Patent
Iwase et al.

(10) Patent No.: US 8,870,377 B2
(45) Date of Patent: Oct. 28, 2014

(54) IMAGE PROCESSING APPARATUS, IMAGE PROCESSING APPARATUS CONTROL METHOD, OPHTHALMOLOGIC APPARATUS, OPHTHALMOLOGIC APPARATUS CONTROL METHOD, OPHTHALMOLOGIC SYSTEM, AND STORAGE MEDIUM

(71) Applicant: Canon Kabushiki Kaisha, Tokyo (JP)

(72) Inventors: Yoshihiko Iwase, Kyoto (JP); Hiroyuki Shinbata, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/743,375

(22) Filed: Jan. 17, 2013

(65) Prior Publication Data

US 2013/0194543 A1 Aug. 1, 2013

(30) Foreign Application Priority Data

Jan. 27, 2012 (JP) .................................. 2012-015930

(51) Int. Cl.
*A61B 3/14* (2006.01)
*A61B 3/00* (2006.01)

(52) U.S. Cl.
USPC .......................................... 351/206; 351/246

(58) Field of Classification Search
USPC .................................................. 351/200–246
See application file for complete search history.

(56) References Cited

U.S. PATENT DOCUMENTS

| 6,244,710 B1 * | 6/2001 | Ogawa ........................... 351/206 |
| 8,137,271 B2 * | 3/2012 | Bille ............................... 600/398 |
| 2013/0093870 A1 | 4/2013 | Shibutani |

FOREIGN PATENT DOCUMENTS

| JP | 2010-125291 A | 6/2010 |
| JP | 2010-201174 A | 9/2010 |
| JP | 2011-212203 A | 10/2011 |
| JP | 2012-100811 A | 5/2012 |
| WO | 2011-122004 A | 10/2011 |

* cited by examiner

*Primary Examiner* — Mohammed Hasan
(74) *Attorney, Agent, or Firm* — Carter, DeLuca, Farrell & Schmidt, LLP

(57) ABSTRACT

An image processing apparatus comprises: a fundus image obtaining unit configured to obtain a fundus image of an eye to be examined; a detection unit configured to detect positions of an optic papilla and macular region of the eye to be examined from the fundus image; and an obtaining position determination unit configured to determine, as an obtaining position where a tomographic image of the optic papilla of the eye to be examined is obtained, a position crossing a line passing through the position of the optic papilla and the position of the macular region.

21 Claims, 9 Drawing Sheets

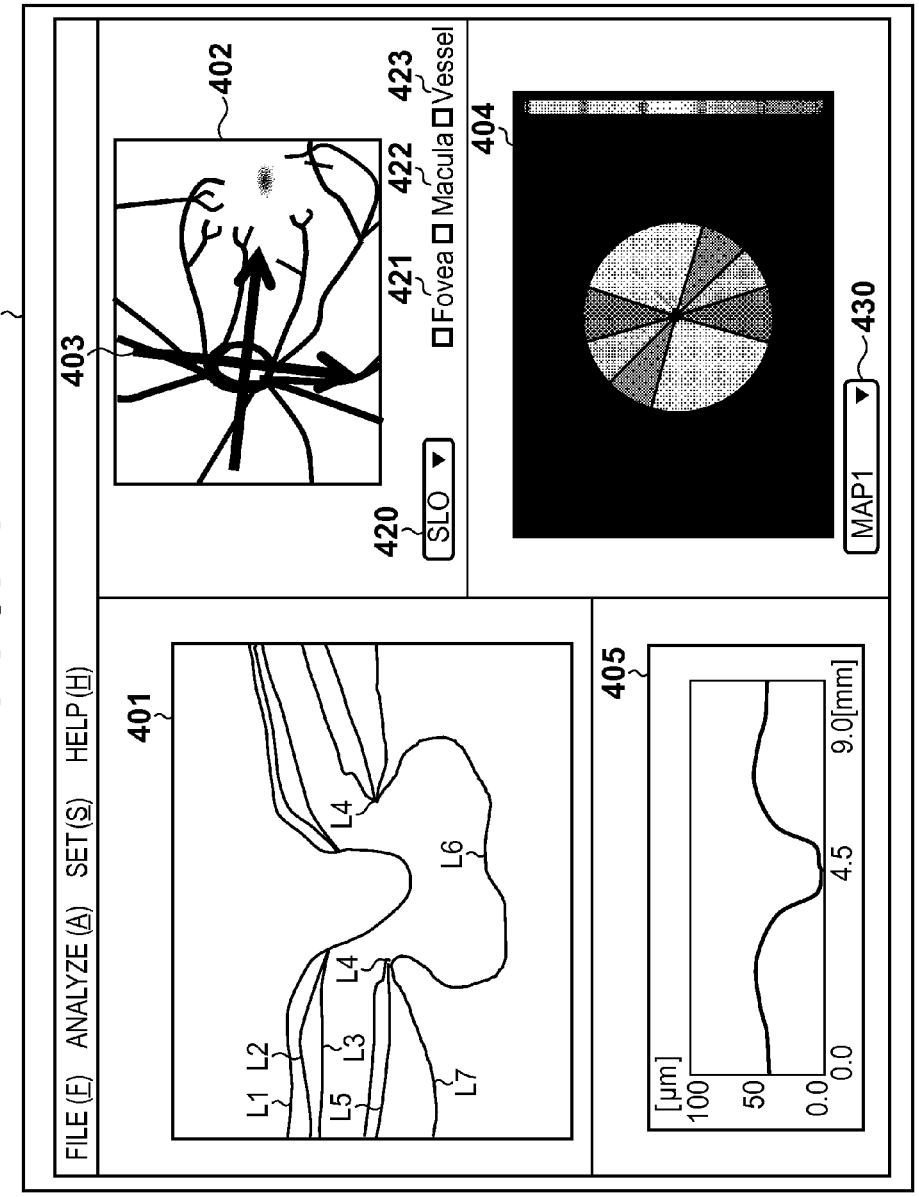

F I G. 9
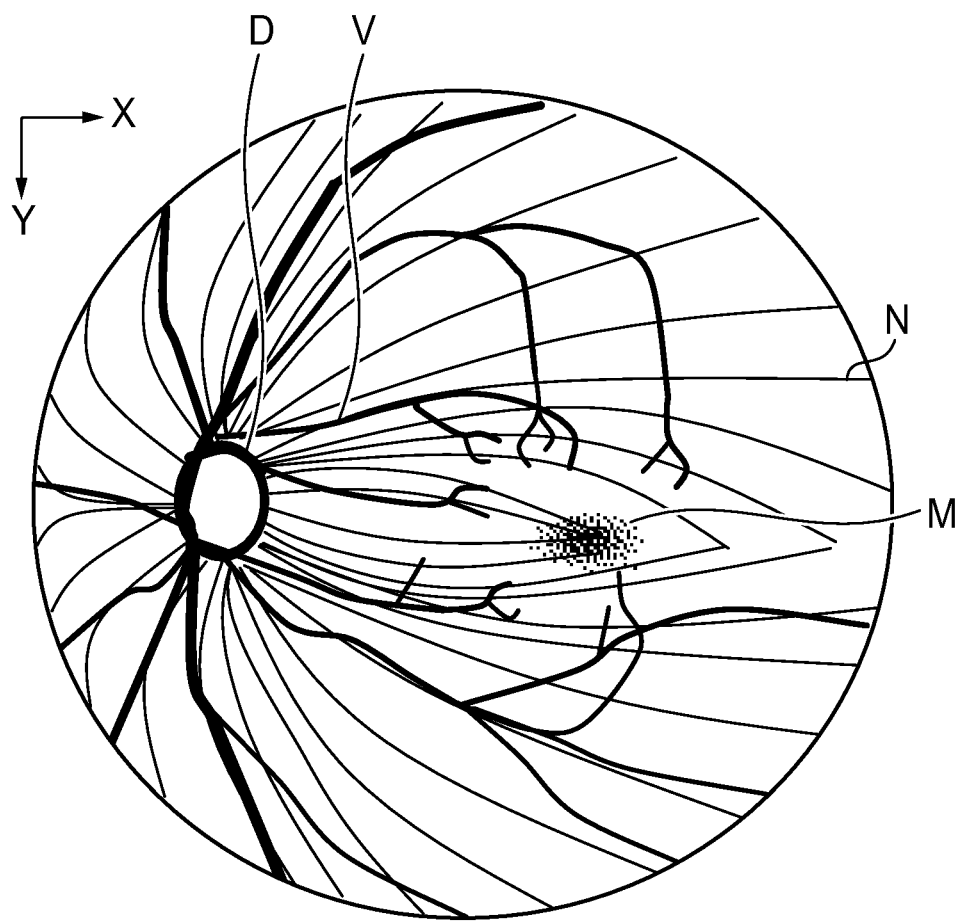

IMAGE PROCESSING APPARATUS, IMAGE PROCESSING APPARATUS CONTROL METHOD, OPHTHALMOLOGIC APPARATUS, OPHTHALMOLOGIC APPARATUS CONTROL METHOD, OPHTHALMOLOGIC SYSTEM, AND STORAGE MEDIUM

BACKGROUND OF THE INVENTION

1. Field of the Invention

The present invention relates to an image processing apparatus, image processing apparatus control method, ophthalmologic apparatus, ophthalmologic apparatus control method, ophthalmologic system, and storage medium.

2. Description of the Related Art

A tomographic imaging apparatus for the eye portion of an eye to be examined, such as an optical coherence tomography (OCT), allows three-dimensionally observing the internal state of a retina layer. The tomographic imaging apparatus has recently received attention because it is useful for more accurately diagnosing a disease. As one form of the OCT, there is known a TD-OCT (Time Domain OCT) which is a combination of a wideband light source and a Michelson interferometer. The TD-OCT is configured to measure interference light with backscattered light from the signal arm by scanning a delay of the reference arm, and obtain depth resolution information. However, high-speed image obtainment is difficult for the TD-OCT. To more quickly obtain an image, an SD-OCT (Spectral Domain OCT) is known as an OCT which uses a wideband light source and obtains an interferogram by a spectrometer. There is also known an SS-OCT (Swept Source OCT) which uses a high-speed wavelength-swept light source as the light source and measures a spectral interference by a single-channel photodetector.

If a morphologic change of the retina can be measured in tomographic images captured by these OCTs, the stage of a disease such as glaucoma, and the degree of recovery after treatment can be quantitatively diagnosed. Conventionally, imaging by the OCT is performed in an apparatus-specific coordinate system. However, for an eye portion, it is desirable to obtain an image considering the course of nerve fibers. FIG. 9 is a schematic view showing the course of nerve fibers. In FIG. 9, each thin curve N represents a nerve fiber, M near the center represents a macular region, an ellipse D represents an optic papilla, and each thick curve V represents a blood vessel.

Japanese Patent Laid-Open No. 2010-125291 discloses a technique of creating a tomographic image along the course of nerve fibers. In Japanese Patent Laid-Open No. 2010-125291, a section along the course of nerve fibers, which is designated by an operator from three-dimensional OCT data captured in an apparatus-specific coordinate system, is created as a tomographic image. Further, imaging is performed along the course of a nerve fiber layer.

To diagnose a disease, sides above and below a nerve fiber to be diagnosed, and its nose and ear sides are desirably captured in one section. However, the technique in Japanese Patent Laid-Open No. 2010-125291 does not guarantee imaging of tomographic images perpendicular and parallel to the course of nerve fibers. For example, the pores of the lamina cribrosa become large in the vertical direction, so a change of the shape readily appears in the vertical direction. Unless imaging is executed in accordance with the coordinate system of the eye portion of each individual, it is hard to obtain an image effective for diagnosis and analysis.

SUMMARY OF THE INVENTION

To solve the above problems, the present invention provides a technique capable of capturing a tomographic image at an imaging position suited to analyze the shape of an eye portion.

According to one aspect of the present invention, there is provided an image processing apparatus comprising: a fundus image obtaining unit configured to obtain a fundus image of an eye to be examined; a detection unit configured to detect positions of an optic papilla and macular region of the eye to be examined from the fundus image; and an obtaining position determination unit configured to determine, as an obtaining position where a tomographic image of the optic papilla of the eye to be examined is obtained, a position crossing a line passing through the position of the optic papilla and the position of the macular region.

Further features of the present invention will be apparent from the following description of exemplary embodiments with reference to the attached drawings.

BRIEF DESCRIPTION OF THE DRAWINGS

FIG. 4 is a view exemplifying an observation display screen according to the first embodiment;

FIG. 9 is a schematic view showing a fundus image representing the course of nerve fibers.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

An ophthalmologic system including an image processing apparatus according to the first embodiment detects an optic papilla and macular region, determines an imaging coordinate system based on their positions, and obtains a tomographic image.

Figure 1:
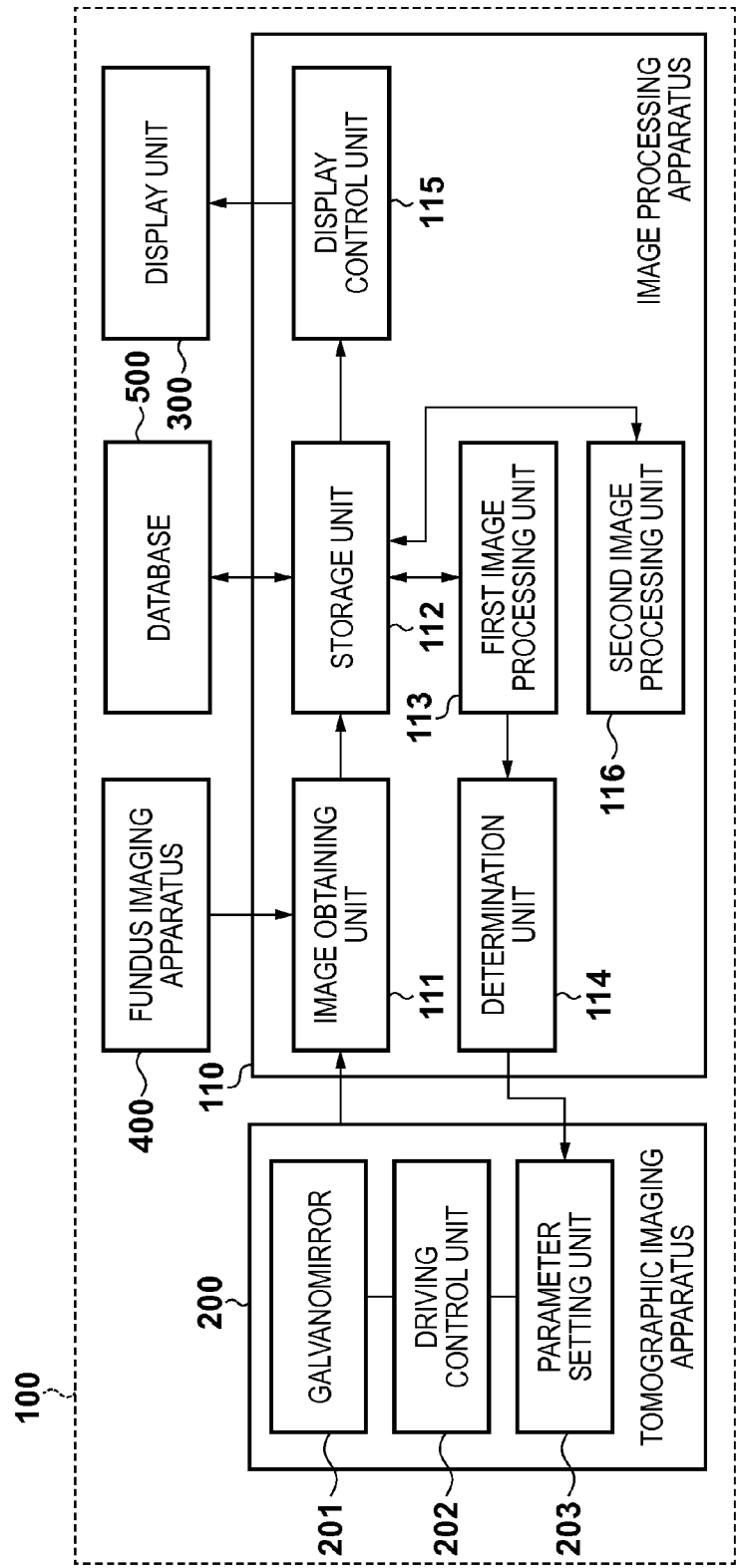
FIG. 1 is a block diagram showing the arrangement of an ophthalmologic system according to the first embodiment.

The ophthalmologic system including the image processing apparatus according to the embodiment will be explained in detail. FIG. 1 shows the arrangement of an ophthalmologic system 100 including an image processing apparatus 110 according to the embodiment. As shown in FIG. 1, the ophthalmologic system 100 includes the image processing apparatus 110, a tomographic imaging apparatus 200, a display unit 300, a fundus imaging apparatus 400, and a database 500. The image processing apparatus 110 is connected to the tomographic imaging apparatus 200, display unit 300, fundus imaging apparatus 400, and database 500 via interfaces. Note that the tomographic imaging apparatus 200 and fundus imaging apparatus 400 may be configured as one ophthalmologic apparatus or single ophthalmologic apparatuses. The tomographic imaging apparatus 200 and image processing apparatus 110 may be configured as one ophthalmologic apparatus.

The tomographic imaging apparatus 200 captures a tomographic image of an eye portion. The tomographic imaging apparatus 200 is, for example, an SD-OCT or SS-OCT. The tomographic imaging apparatus 200 includes a galvanomirror 201, driving control unit 202, and parameter setting unit 203. Note that the tomographic imaging apparatus 200 is a well-known apparatus, and a detailed description thereof will be omitted. Here, a function of setting scanning line parameters in accordance with an instruction from the image processing apparatus 110 will be mainly explained.

The galvanomirror 201 scans a fundus with measurement light, and defines the OCT imaging range of the fundus. The driving control unit 202 controls the driving range and speed of the galvanomirror 201, and defines the imaging range and scanning line count (scanning speed within the plane) within the plane on the fundus. The galvanomirror is described as one mirror for simplicity. In practice, the galvanomirror is formed from two mirrors for X scanning and Y scanning, and can scan a desired range on the fundus with measurement light.

The parameter setting unit 203 sets various parameters used to control the operation of the galvanomirror 201 by the driving control unit 202. Imaging conditions in tomographic imaging by the tomographic imaging apparatus 200 are determined in accordance with parameters set by the parameter setting unit 203. More specifically, the scanning position of a scanning line, the scanning line count, the imaging count, and the like, which are set in accordance with an instruction from the image processing apparatus 110, are determined.

The display unit 300 displays a captured tomographic image and fundus image. The fundus imaging apparatus 400 is an apparatus which captures the fundus image of an eye portion. This apparatus is, for example, a fundus camera or SLO.

The image processing apparatus 110 includes an image obtaining unit 111, storage unit 112, first image processing unit 113, determination unit 114, display control unit 115, and second image processing unit 116.

The image obtaining unit 111 functions as a tomographic image obtaining unit which obtains a tomographic image captured by the tomographic imaging apparatus 200. The image obtaining unit 111 also functions as a fundus image obtaining unit which obtains a fundus image captured by the fundus imaging apparatus 400. The image obtaining unit 111 stores the obtained images in the storage unit 112. The first image processing unit 113 detects an optic papilla and macular region from the fundus image stored in the storage unit 112. The determination unit 114 determines a reference coordinate system based on the result of detection by the first image processing unit 113 (coordinate system determination). The determination unit 114 determines a tomographic image obtaining position based on the reference coordinate system, and outputs it as an imaging parameter to the parameter setting unit 203 of the tomographic imaging apparatus 200. The display control unit 115 controls the display unit 300 to display various images. The second image processing unit 116 extracts each region of a retina layer from the tomographic image stored in the storage unit 112, and performs calculation of the thickness of the retina layer, extraction of a lamina cribrosa, analysis of the shape of the extracted lamina cribrosa, and the like.

Figure 2:
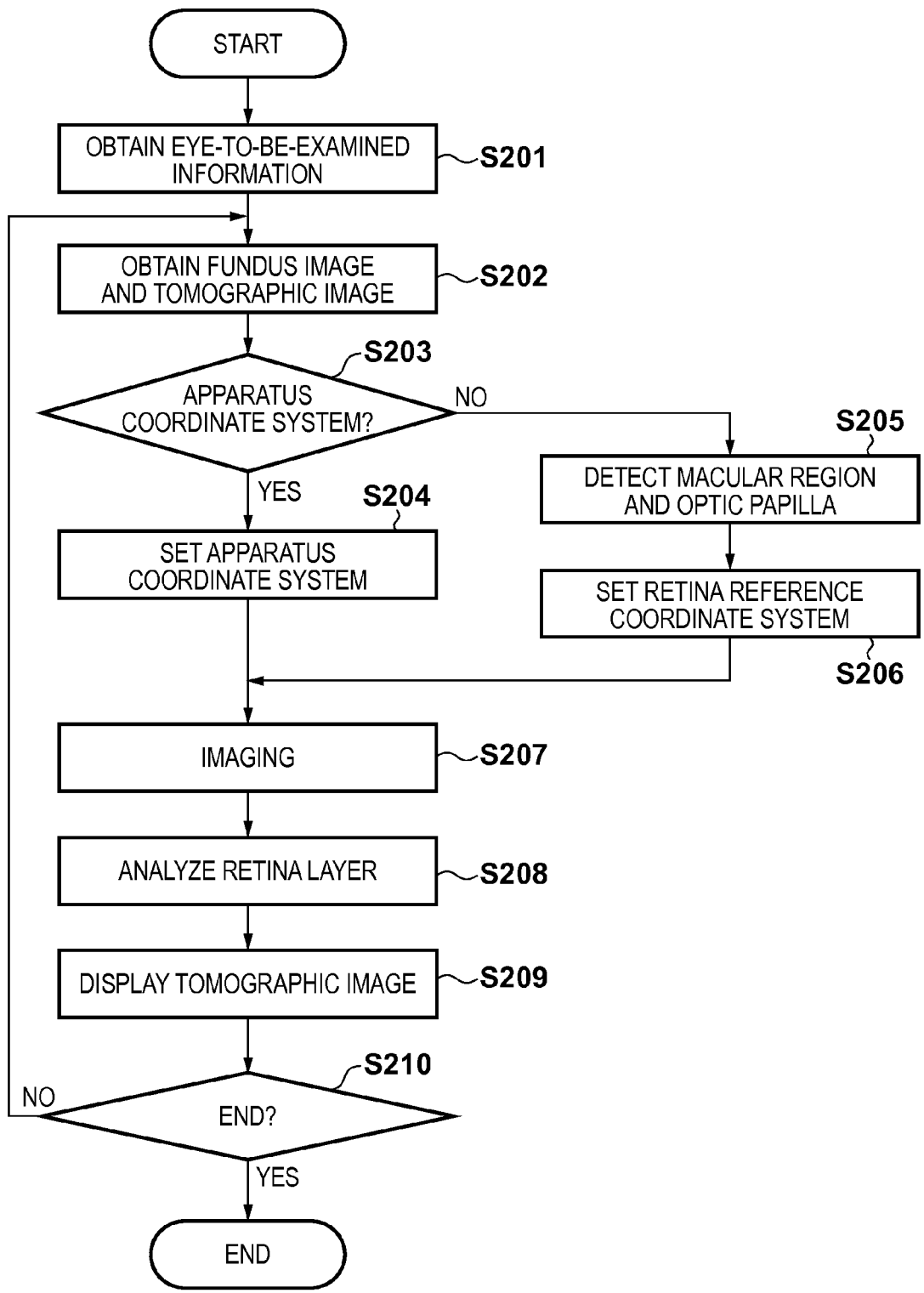
FIG. 2 is a flowchart showing a processing sequence in an image processing apparatus according to the first embodiment.
Figure 3:
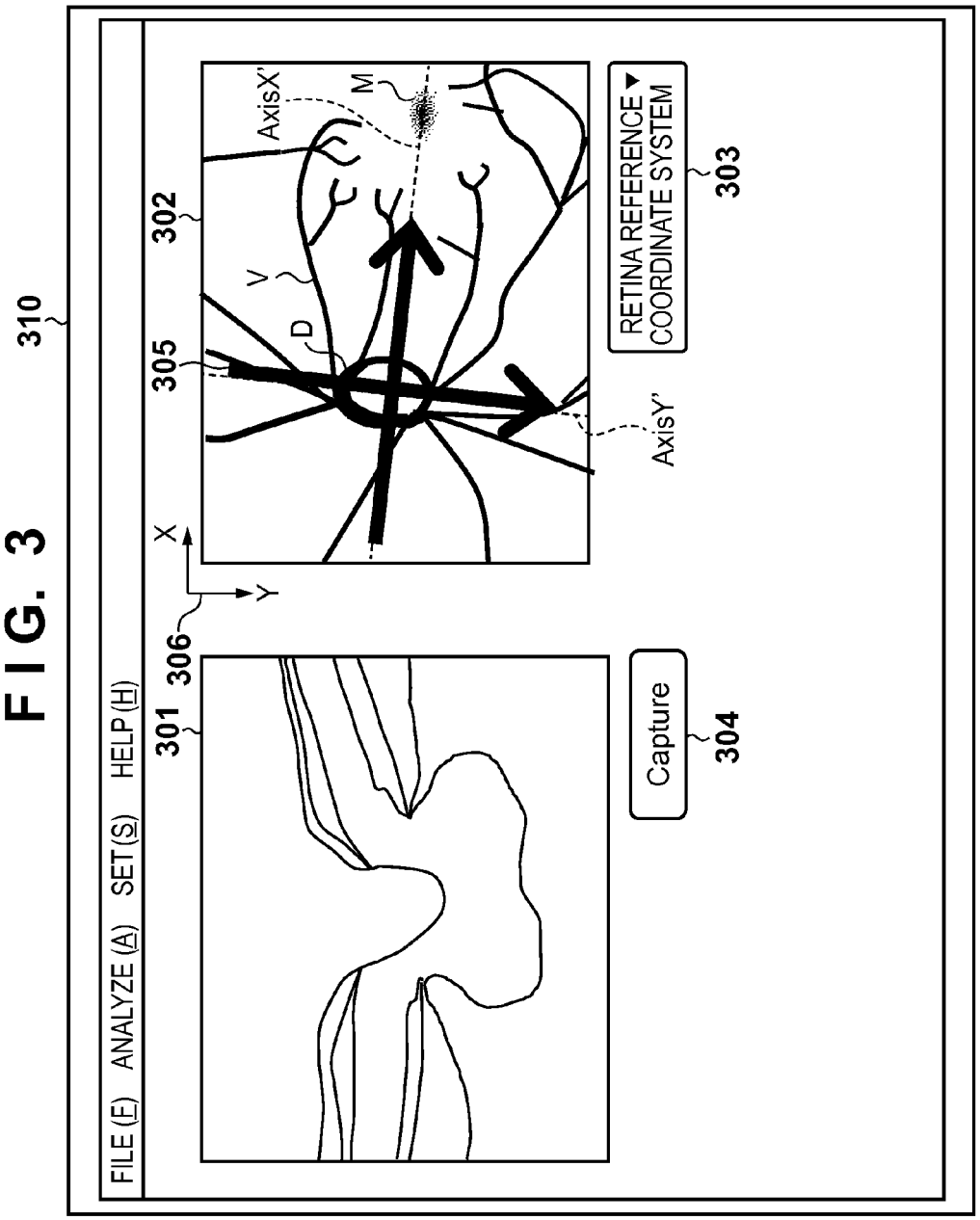
FIG. 3 is a view exemplifying an imaging display screen according to the first embodiment.

Processing procedures by the image processing apparatus 110 according to the embodiment will be described with reference to FIGS. 2 and 3. FIG. 2 is a flowchart showing a processing sequence in the first embodiment. FIG. 3 exemplifies a display screen in imaging that is displayed on the display unit 300 in the first embodiment. Referring to FIG. 3, a tomographic imaging screen 310 includes a tomographic image 301, fundus image 302, imaging coordinate system setting combo box 303, and imaging instruction button 304. An imaging region 305 is a region superimposed and displayed on the fundus image 302. Coordinate axes 306 are coordinate axes which are uniformly set regardless of an individual difference. M represents a macular region, D represents an optic papilla, and V represents a blood vessel.

When there are a plurality of imaging modes, imaging of user's choice starts upon selecting a mode for performing imaging which meets the purpose. For example, in the embodiment, selection of an imaging mode in which a tomographic image containing the lamina cribrosa region of an eye to be examined is obtained is received in accordance with a user operation or the like. Processing in the embodiment starts upon receiving the imaging mode in which a tomographic image containing the lamina cribrosa region of an eye to be examined is obtained.

<Step S201<

In step S201, an eye-to-be-examined information obtaining unit (not shown) externally obtains an object identification number as information for identifying an eye to be examined. Based on the object identification number, the eye-to-be-examined information obtaining unit obtains information (for example, the name, age, and sex of a patient) about the eye to be examined that is held in the database 500, and stores it in the storage unit 112.

<Step S202>

In step S202, the image obtaining unit 111 performs processing to obtain a preview image to be displayed on the tomographic imaging screen 310 of FIG. 3, and an image used for portion detection in step S205. More specifically, the image obtaining unit 111 obtains a fundus image from the fundus imaging apparatus 400, and obtains a tomographic image from the tomographic imaging apparatus 200. The fundus image contains the macular region M and optic papilla D.

<Step S203>

In step S203, the display control unit 115 receives selection of an imaging coordinate system by receiving a user operation to the imaging coordinate system setting combo box 303. The imaging coordinate system setting combo box 303 allows selecting and setting a retina reference coordinate system or apparatus coordinate system as the imaging coordinate system. The retina reference coordinate system is a coordinate system which is configured using, as the reference, a line connecting the macular region M and the optic papilla D. If the apparatus coordinate system is set (YES in step S203), the process advances to step S204; if the retina reference coordinate system is set (NO in step S203), to step S205.

<Step S204>

In step S204, the determination unit 114 sets a predetermined apparatus coordinate system. More specifically, the determination unit 114 sets, in the parameter setting unit 203 of the tomographic imaging apparatus 200, information representing that the apparatus coordinate system has been selected, and information representing an obtaining position determined using the apparatus coordinate system as the reference. The information representing an obtaining position contains the imaging range and imaging direction. In the apparatus coordinate system, when an eye to be examined is imaged, the horizontal direction is defined as the X-axis, and the vertical direction is defined as the Y-axis. These coordinate axes are uniformly set regardless of an individual difference, as indicated by the coordinate axes 306 of FIG. 3. To the contrary, the retina reference coordinate system is a coordinate system which is set based on the anatomical features of an eye portion. The coordinate axes of the retina reference coordinate system are set in accordance with an individual difference and imaging situation. A case in which the retina reference coordinate system is set will be explained with reference to steps S205 and S206.

<Step S205>

In step S205, the first image processing unit 113 detects the position of the macular region M and that of the optic papilla D from the fundus image. First, detection of the optic papilla D will be exemplified. It is known that the pixel value of the optic papilla D is large (bright) in a fundus image. Thus, the color distribution is checked, and the center of a bright region (optic papilla) in the image is set as the center of the optic papilla. Alternatively, since blood vessels concentrate at the optic papilla, blood vessels may be detected from a fundus image to detect the optic papilla using the information. As the blood vessel detection method, for example, a blood vessel is extracted using a filter which emphasizes a linear structure because the blood vessel has a thin linear structure. The filter which emphasizes a linear structure is, for example, a filter which calculates the difference between the average of image density values within a line segment assumed as a structural element and the average of image density values within a local region surrounding the structural element. However, the filter is not limited to this, and may be a difference filter such as a Sobel filter. Alternatively, the eigenvalues of a Hessian matrix may be calculated for the respective pixels of a density value image, and a linear region may be extracted from combinations each of two eigenvalues obtained as results. Further, a top-hat operation which simply uses a line segment as a structural element may be performed. Blood vessel positions detected by these methods, and the bright region of the optic papilla are combined, detecting the center of the optic papilla.

Next, detection of the fovea centralis at the center of the macular region M will be exemplified. It is known that the pixel value of the macular region M is small (dark) in a fundus image. From this, the color distribution of a fundus image is checked, and the center of a dark region (macular region) in the image is set as the fovea centralis at the center of the macular region M. Blood vessels sometimes have the same color distribution as that of the macular region. However, the blood vessel has a thin linear structure, as described above, so the linear structure and circular structure can be discriminated from each other. Also, a rough macular region can be estimated using the position of the optic papilla D and the anatomical feature of the dendriform structure of the blood vessel. Using these pieces of information can reduce detection errors in macular region detection.

<Step S206>

In step S206, the determination unit 114 determines a retina reference coordinate system in the fundus image based on a line passing through the fovea centralis at the center of the macular region M and the optic papilla D that have been detected by the first image processing unit 113. As shown in FIG. 3, the center of the optic papilla D is defined as the origin of the retina reference coordinate system, and the first axis is obtained as a broken line AxisX' passing through the center of the optic papilla D and that of the macular region M. Then, the second axis of the retina reference coordinate system is obtained as a broken line AxisY' crossing (for example, orthogonal to) AxisX' at the origin. That is, the retina reference coordinate system is often a coordinate system which is rotated by the angle θ from the apparatus coordinate system. Note that the line passing through the position of the optic papilla and that of the macular region, and the line crossing (for example, orthogonal to) this line may be actually displayed or may not be displayed. The line passing through the position of the optic papilla and that of the macular region, and a display form representing a tomographic image obtaining position may be superimposed on a fundus image and displayed on the display unit 300. A display form representing orthogonality may be displayed on the display unit 300. The display form representing orthogonality may be a text or the like, or a mark representing orthogonality may be displayed on a fundus image.

Displaying these lines is convenient because the user can determine a tomographic image obtaining position while confirming the positions of these lines on a fundus image when he looks at a preview screen (screen for adjusting a tomographic image obtaining position). By using axes based on these coordinate axes as the reference, the determination unit 114 determines the imaging region 305 representing a tomographic image obtaining position. Then, the determination unit 114 determines, as an obtaining position where a tomographic image of the optic papilla of an eye to be examined is obtained, a position crossing the line passing through the position of the optic papilla and that of the macular region. Alternatively, a region scanned on the axis at a predetermined width by a predetermined distance may be set as the imaging region 305. The position of the imaging region 305 may be determined in accordance with a user operation by using the coordinate axes of the retina reference coordinate system as the reference. The determination unit 114 sets information representing the rotation angle θ of the retina reference coordinate system and information representing the obtaining position by outputting them as imaging parameters to the parameter setting unit 203 of the tomographic imaging apparatus 200. Note that the embodiment has explained a coordinate system using the center of the optic papilla D as the origin. However, the origin is not limited to this. For example, the present invention may adopt a coordinate system using the center of the macular region M as the origin. Even in this case, since only the origin position is different and the rotation angle θ of the coordinate system remains unchanged, the present invention is applicable.

<Step S207>

In step S207, the tomographic imaging apparatus 200 controls the driving control unit 202 based on the imaging parameters set in the parameter setting unit 203 to set the imaging region of the galvanomirror 201 and capture a tomographic image. The galvanomirror 201 is formed from an X scanner for the horizontal direction and a Y scanner for the vertical direction. By respectively changing the orientations of these scanners, the galvanomirror 201 can be scanned in the horizontal direction (X) and vertical direction (Y) in the apparatus coordinate system. By simultaneously changing the orientations of these scanners, the galvanomirror 201 can be scanned in a composite direction of the horizontal and vertical directions. The galvanomirror 201 can therefore be scanned in an arbitrary direction on the fundus plane. When the retina reference coordinate system is selected and the rotation angle θ is set for the apparatus coordinate system, the driving control unit 202 controls the X and Y scanners in accordance with the angle θ.

<Step S208>

Figure 5A:
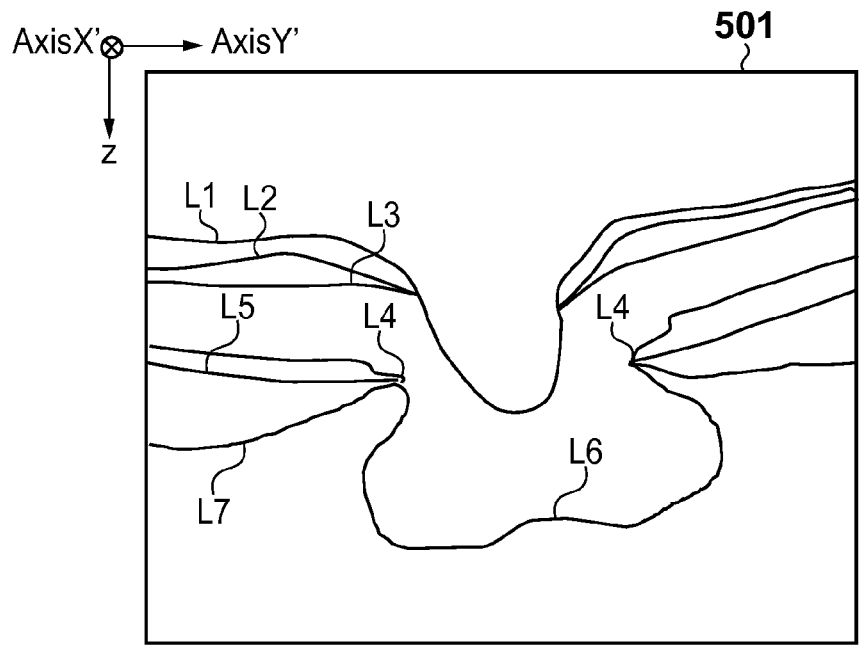
FIGS. 5A and 5B are schematic views each showing a tomographic image of the optic papilla of a retina according to the first embodiment.

In step S208, the second image processing unit 116 extracts a retina layer from the tomographic image stored in the storage unit 112, and analyzes it. First, extraction of the boundaries between the respective regions of the retina layer for the optic papilla will be explained with reference to FIG. 5A. FIG. 5A shows a vertical tomographic image 501 captured in the retina reference coordinate system. FIG. 5A shows a tomographic image of the optic papilla. L1 represents an inner limiting membrane (ILM), L2 represents a nerve fiber layer (NFL), L3 represents a ganglion cell layer (GCL), L4 represents a Bruch's membrane opening (BMO), L5 represents a retinal pigment epithelium layer (RPE), L6 represents a lamina cribrosa (LC), and L7 represents a choroid. The second image processing unit 116 extracts the boundaries between the respective regions L1 to L7.

First, the second image processing unit 116 applies a median filter and Sobel filter to the tomographic image 501, generating images (the generated images will be referred to as a median image and Sobel image, respectively). Then, the second image processing unit 116 generates profiles for each A-scan from the generated median image and Sobel image. A luminance value profile is generated from the median image, and a gradient profile is generated from the Sobel image. Peaks in the profile generated from the Sobel image are extracted. By referring to the profile of the median image before and after each extracted peak or at an interval between peaks, the boundaries between the respective regions of the retina layer are extracted. Thicknesses are analyzed from the extracted layer boundaries. For example, assume that the ILM L1 and the boundaries of the NFL L2 and GCL L3 are extracted. In this case, the thickness of the NFL L2 is calculated. The layer thickness can be calculated by obtaining the difference between the Z-coordinate of the inner limiting membrane L1, and those of the boundaries of the NFL L2 and GCL L3 at each AxiY'-coordinate on the AxisY'-Z plane. Not only the thickness but also the layer area or volume may be obtained. The area of the NFL L2 can be calculated by adding layer thicknesses at respective coordinate points along the X-axis on one tomographic image. The volume of the NFL L2 can be calculated by adding obtained areas along the Y-axis. Although calculation of the NFL L2 has been exemplified, the thicknesses, areas, and volumes of the remaining layers and the entire retina layer can be obtained in the same manner.

Figure 5B:
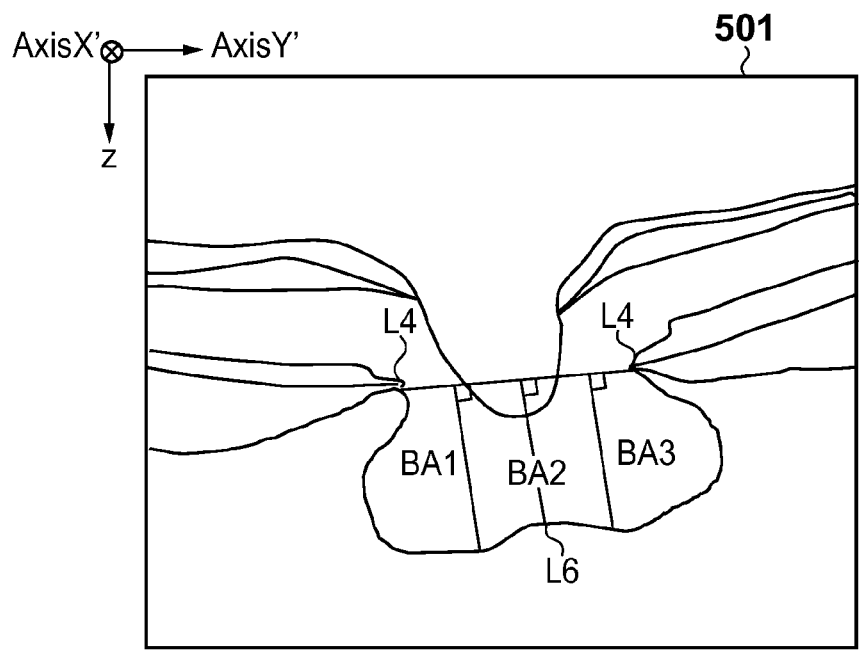

Next, extraction and analysis of the shape of the lamina cribrosa will be explained with reference to FIG. 5B. To extract the lamina cribrosa region, the second image processing unit 116 extracts the BMO L4 from the tomographic image 501 in FIG. 5B. The BMO L4 is extracted by, for example, specifying the cup of the optic papilla by using the ILM L1 and RPE L5 extracted in step S208. In the embodiment, first, the vicinity of the center of the cup of the optic papilla is specified. The cup of the optic papilla has a feature in which the RPE L5 does not exist, and a feature in which the shape of the ILM L1 has a large gradient in the direction of depth (Z direction in FIG. 5B). Considering this, a local region containing each A-scan and its peripheral A-scans is set, the presence of the RPE L5 in the local region is checked, and the gradient of the ILM L1 in the direction of depth is calculated, specifying a point near the center of the cup of the optic papilla. Then, points of the RPE L5 near the center of the cup of the optic papilla in respective tomographic images are connected in all tomographic images, setting an RPE region which has an elliptic shape when viewed from the C-scan direction. The position of this region is set as an initial position, and a dynamic contour model such as Snakes or Level Set is applied, specifying the BMO L4 in each tomographic image. After that, the edge component is traced from the specified BMO end toward the center of the cup of the optic papilla, specifying the accurate position of the BMO end. In the embodiment, first, a coordinate value and edge component are checked for each BMO end. Then, the position of each BMO end is set as the start point, and the edge is traced toward the center of the cup of the optic papilla. In tracing, by referring to an edge component at the position of each BMO end, the search point is updated to a position closest to an edge component present inward, and the reference edge component is also updated. By repeating this operation, an accurate BMO end is specified. On one tomographic image (B-scan), a lamina cribrosa boundary using the BMO L4 as a fixed end is set as an initial value at portions where two points of the BMO L4 are extracted. A dynamic contour model such as Snakes or Level Set is executed, extracting the lamina cribrosa region (L6 in FIG. 5B). The dynamic contour model may further use a probability atlas, and region detection may be performed using the spatial existence probability of the lamina cribrosa. Note that automatic extraction of the lamina cribrosa region has been exemplified. Alternatively, the operator may correct the automatic extraction result using an operation unit (not shown), or manually set a lamina cribrosa.

Next, analysis of the shape of the lamina cribrosa by Bowing Angle will be explained. The Bowing Angle analysis method will be explained. First, two points of the BMO L4 are connected by a straight line, and the straight line is divided into four. Perpendiculars BA1, BA2, and BA3 are drawn from the division points to the lamina cribrosa. Bowing Angle can be obtained by solving equation (1) using the lengths of these perpendiculars:

$$BowingAngle = BA2 - \frac{BA1 + BA3}{2} \quad (1)$$

In equation (1), the numerical values of the lengths (distances) of the respective perpendiculars are substituted into BA1, BA2, and BA3. In equation (1), a larger (positive) numerical value indicates a shape which is convex downward much more, and a smaller (negative) numerical value indicates a shape which comes closer to the W shape. That is, Bowing Angle is an index which allows grasping the shape of the lamina cribrosa from the sign and numerical value.

Bowing Angle may be calculated not as a numerical value but as a ratio. An expression in this case is equation (2):

$$BowingAngleRatio = BA2 \Big/ \left(\frac{BA1 + BA3}{2}\right) \quad (2)$$

In equation (2), a Bowing Angle ratio of 1 or more indicates a shape which is convex downward, and a Bowing Angle ratio of smaller than 1 indicates the W shape.

<Step S209>

In step S209, the display control unit 115 displays the tomographic image on the display unit 300. FIG. 4 exemplifies a display screen displayed on the display unit 300. A tomographic image observation screen 410 includes a tomographic image 401, fundus image 402, analysis map 404, and analysis graph 405. In this manner, a display form representing the analysis result (shape of the extracted lamina cribrosa) is displayed together with the tomographic image.

The tomographic image 401 is an image obtained by superimposing and displaying, on a captured tomographic image, the segmentation results (L1 to L6) of extracting the respective layers of the retina layer. A region 403 indicates the obtaining position of the tomographic image and its coordinate system. The analysis map 404 is a map obtained by analyzing the tomographic image by the second image processing unit 116. The analysis graph 405 is a graph obtained by analyzing the tomographic image by the second image processing unit 116. A combo box 420 is a box for selecting the type of fundus image. A combo box 430 is a box for selecting the type of map of the analysis result.

Check boxes 421 to 423 are used when displaying an optic papilla (Fovea), macular region (Macula), and blood vessel (Vessel) detected by the first image processing unit 113. For example, when the check boxes 421 to 423 are checked, the positions of the optic papilla (Fovea), macular region (Macula), and blood vessel (Vessel) can be superimposed and displayed on the fundus image 402. In FIG. 4, one check box is prepared for each portion. However, it is also possible to integrate the check boxes into one, and switch display/non display of pieces of information corresponding to the check boxes 421 to 423 by selecting one check box.

<Step S210>

In step S210, an instruction obtaining unit (not shown) externally obtains an instruction about whether to end capturing of a tomographic image by the ophthalmologic system 100. The operator inputs this instruction using an operation unit (not shown). If the instruction obtaining unit has obtained the instruction to end the processing (YES in step S210), the ophthalmologic system 100 ends the processing. If capturing continues without ending the processing (NO in step S210), the ophthalmologic system 100 returns the process to step S202 to continue capturing. In this way, the processing of the ophthalmologic system 100 is executed.

As described above, the first embodiment can provide an image processing apparatus which determines an imaging coordinate system based on the optic papilla (first position) and the macular region (second position), and performs imaging in a coordinate system suited to analyze the shape of an eye portion. Imaging can be executed in directions perpendicular and parallel to the course of nerve fibers, while coping with an individual difference. By taking account of the features of an eye portion, imaging is performed based on the course of nerve fibers. Thus, a tomographic image can be captured at a position suitable for analysis or diagnosis.

Note that the embodiment has used the optic papilla and macular region. However, the present invention is not limited to these portions, and another portion may be used as long as the portion is so characteristic as to specify its position. As the above-mentioned user operation, the user may operate a mouse or the like (not shown) to move the cursor and make a selection, and then processing of his choice may be received. Alternatively, processing may be received via a touch panel.

Second Embodiment

The first embodiment has exemplified a case in which the operator selects the apparatus coordinate system or retina reference coordinate system. To the contrary, the second embodiment will explain an example in which an image processing apparatus determines an imaging coordinate system based on the result of a previous analysis status in follow-up.

Figure 6:
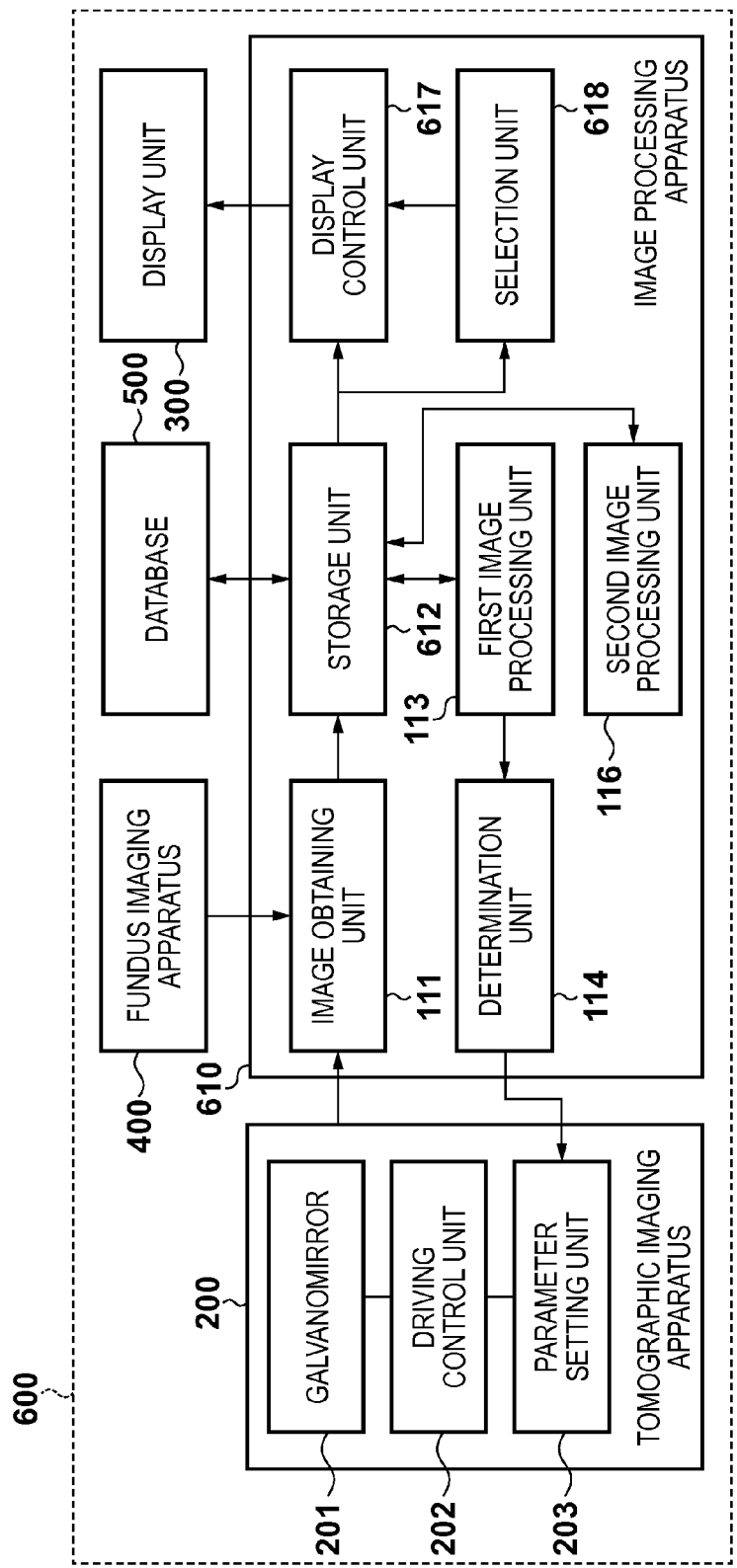
FIG. 6 is a block diagram showing the arrangement of an ophthalmologic system according to the second embodiment.

FIG. 6 shows the arrangement of an ophthalmologic system 600 including an image processing apparatus 610 according to the second embodiment. As shown in FIG. 6, the image processing apparatus 610 includes an image obtaining unit 111, storage unit 612, first image processing unit 113, determination unit 114, display control unit 615, second image processing unit 116, and selection unit 617. The selection unit 617 selects an imaging coordinate system based on a previous analysis result. Note that a description of processing units having the same functions as those in the first embodiment will not be repeated.

Figure 7:
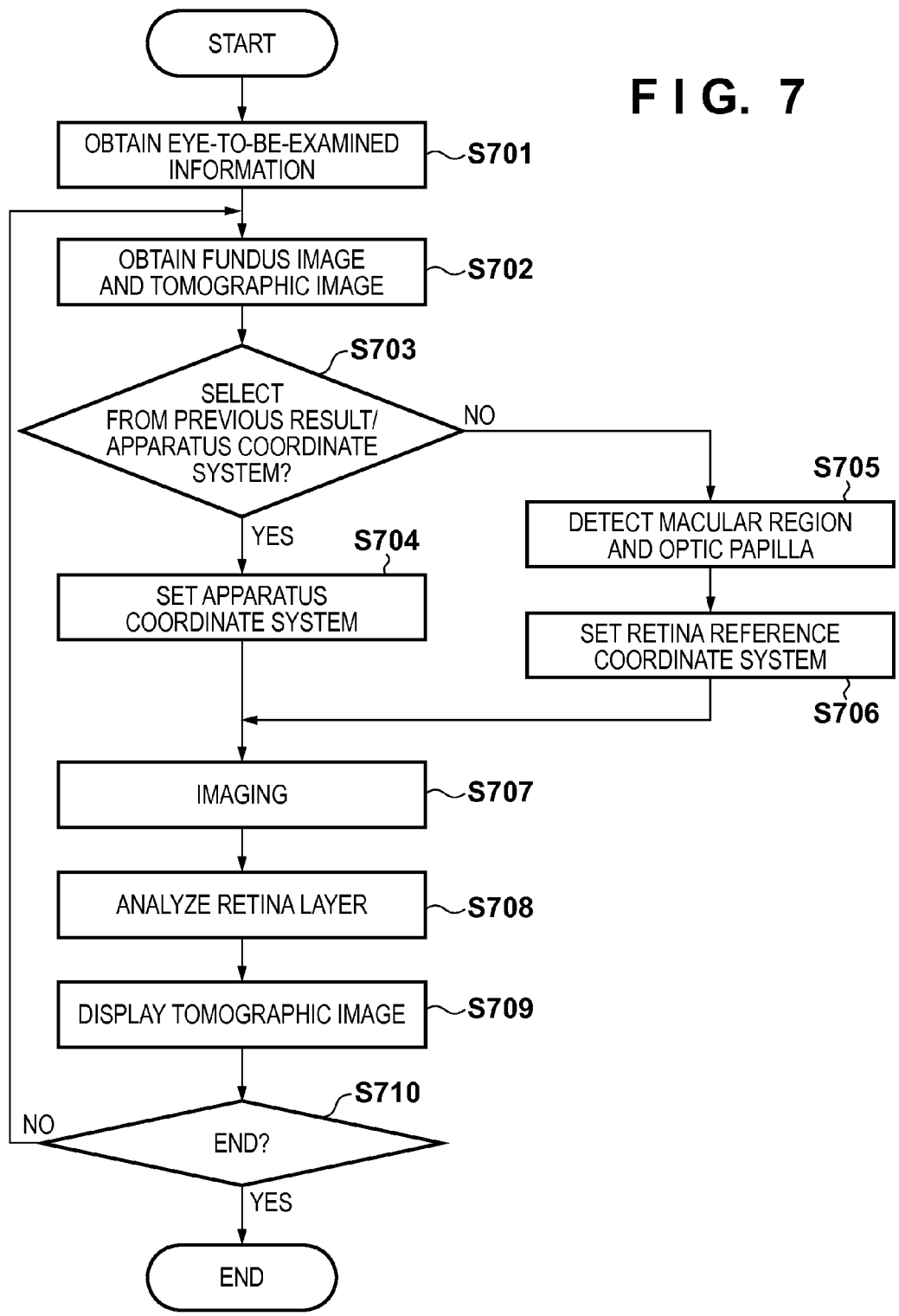
FIG. 7 is a flowchart showing a processing sequence in an image processing apparatus according to the second embodiment.

Processing procedures by the image processing apparatus 610 according to the second embodiment will be described with reference to FIGS. 7 and 8. Note that steps other than steps S701 and S703 are the same as those in the first embodiment, and a description thereof will not be repeated.

<Step S701>

In step S701, an eye-to-be-examined information obtaining unit (not shown) externally obtains an object identification number as information for identifying an eye to be examined. Based on the object identification number, the eye-to-be-examined information obtaining unit obtains information (for example, the name, age, and sex of a patient) about the eye to be examined that is held in a database 500. If there is a past imaging record, the eye-to-be-examined information obtaining unit obtains information (for example, past analysis result) about past tomography of the eye to be examined. The eye-to-be-examined information obtaining unit stores the obtained information in the storage unit 612.

<Step S703>

In step S703, the selection unit 617 selects an imaging coordinate system based on the past imaging record and analysis result. For example, when the vertical symmetry of a nerve fiber layer is lost from the past analysis result, the display control unit 615 displays the retina reference coordinate system as an initial state in an imaging coordinate system setting combo box 803 in FIG. 8. Alternatively, the display control unit 615 displays, in a message display box 807, a message which prompts imaging in the retina reference coordinate system. In the determination of the vertical symmetry of a nerve fiber layer, thicknesses of the nerve fiber layer in the vertical direction are compared using the center of a previous imaging region as the reference along the Y-axis of a fundus image in FIG. 8. If the thickness difference is equal to or larger than a threshold, it is determined that the vertical symmetry is abnormal.

As another example, the selection unit 617 compares measurement results of Bowing Angle (value representing the shape of a lamina cribrosa) in the horizontal and vertical directions, which are lamina cribrosa analysis results, and determines the vertical symmetry based on the difference. Instead, a Bowing Angle measurement value in the vertical direction is compared with a normal Bowing Angle database created from a plurality of normal eyes. If the measurement value deviates from the normal database by a threshold or more, the retina reference coordinate system is set as an initial state in the imaging coordinate system setting combo box 803 in FIG. 8. Alternatively, a message which prompts imaging in the retina reference coordinate system is displayed in the message display box 807.

Figure 8:
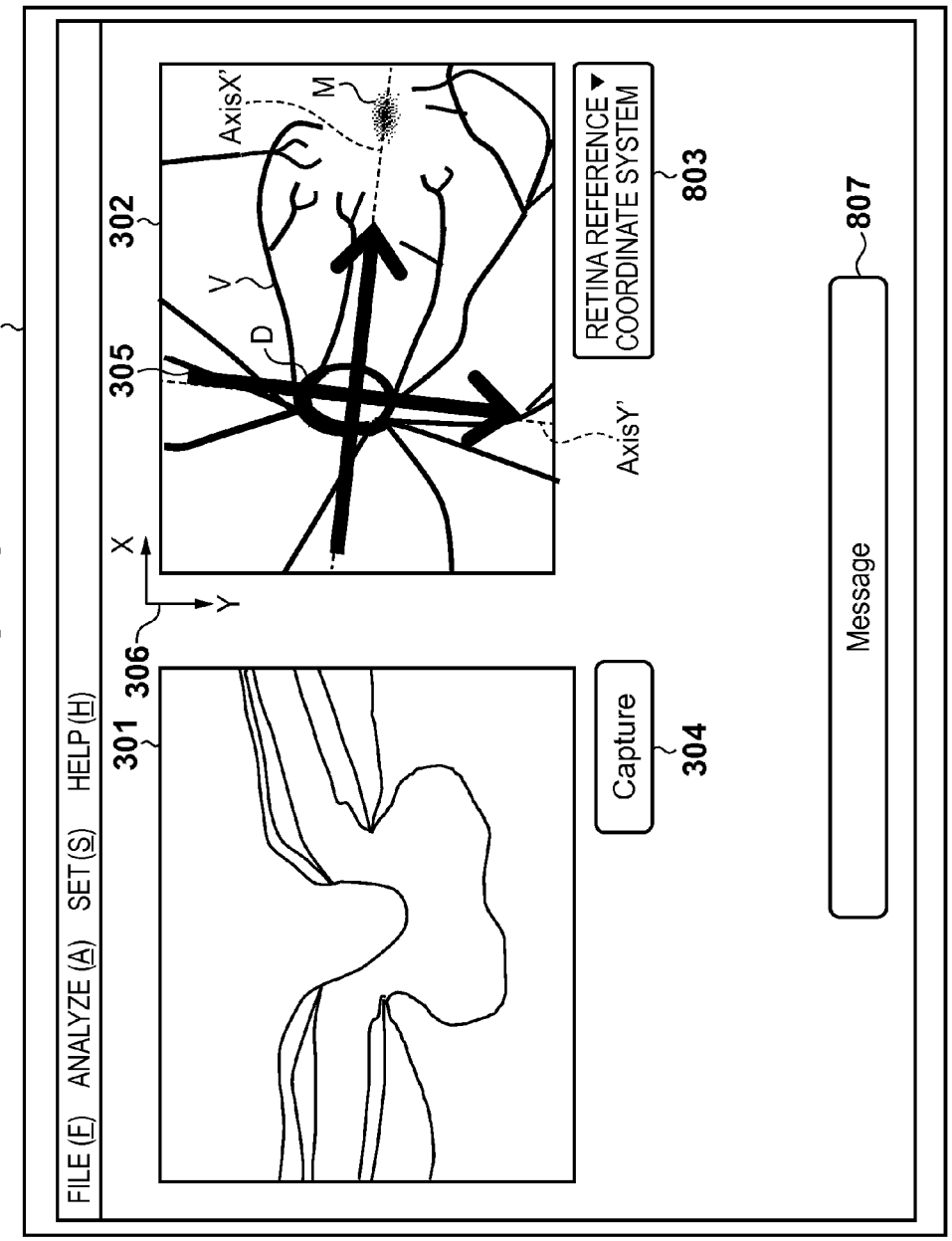
FIG. 8 is a view exemplifying an imaging display screen according to the second embodiment.

As still another example, when the diagnosis result of an eye to be examined indicates glaucoma or suspected glaucoma based on eye-to-be-examined information obtained by the eye-to-be-examined information obtaining unit, the selection unit 617 sets the retina reference coordinate system as an initial state in the imaging coordinate system setting combo box 803 in FIG. 8. Alternatively, a message which prompts imaging in the retina reference coordinate system is displayed in the message display box 807. As described above, in follow-up, the operator is prompted to perform imaging in an imaging coordinate system based on the optic papilla and macular region. In response to this, the operator sets retina reference coordinates and performs imaging. Since imaging can be executed in directions perpendicular and parallel to the course of nerve fibers, a tomographic image can be captured at a position suitable for analysis or diagnosis.

The present invention allows capturing a tomographic image at an imaging position suited to analyze the shape of an eye portion.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-015930, filed on Jan. 27, 2012, which is hereby incorporated by reference herein in its entirety.

What is claimed is:

1. An image processing apparatus comprising:
a fundus image obtaining unit configured to obtain a fundus image of an eye to be examined;
a detection unit configured to detect a position of an optic papilla region and a position of macular region of the eye to be examined from the fundus image; and
an obtaining position determination unit configured to determine, as an obtaining position where a tomographic image of the optic papilla region of the eye to be examined is obtained, a position crossing a line passing through the position of the optic papilla region and the position of the macular region.

2. The apparatus according to claim 1, further comprising a display control unit configured to control a display unit to display, on the fundus image, the line passing through the position of the optic papilla region and the position of the macular region, and a display form representing the obtaining position.

3. The apparatus according to claim 2, wherein the obtaining position determination unit determines, as the obtaining position, a position orthogonal to the line passing through the position of the optic papilla region and the position of the macular region, and
wherein the display control unit controls the display unit to display a display form representing the orthogonality.

4. The apparatus according to claim 1, further comprising:
an extraction unit configured to extract a lamina cribrosa from the tomographic image obtained at the obtaining position; and
a display control unit configured to control a display unit to display, together with the tomographic image, a display form representing a shape of the extracted lamina cribrosa.

5. The apparatus according to claim 1, further comprising:
an extraction unit configured to extract a lamina cribrosa from the tomographic image based on the line passing through the position of the optic papilla region and the position of the macular region, and the position crossing the line; and
a determination unit configured to determine vertical symmetry for the lamina cribrosa extracted by the extraction unit, based on a difference between a value representing a shape of the lamina cribrosa along the line, and a value representing a shape of the lamina cribrosa in a direction crossing the line.

6. The apparatus according to claim 5, further comprising a selection reception unit configured to receive selection of one of a preset apparatus coordinate system and a reference coordinate system,
wherein in a case where the apparatus coordinate system is selected via the selection reception unit, the obtaining position determination unit determines a tomographic image obtaining position based on the apparatus coordinate system.

7. The apparatus according to claim 1, further comprising a reception unit configured to receive selection of an imaging mode,
wherein in a case where the reception unit receives an imaging mode in which a tomographic image containing a lamina cribrosa region of the eye to be examined is obtained, the fundus image obtaining unit obtains a fundus image containing the optic papilla region and the macular region.

8. The apparatus according to claim 1, further comprising:
a coordinate system determination unit configured to determine a reference coordinate system in which the optic papilla region is set as an origin, an axis passing through the optic papilla region and the macular region is set as a first axis, and an axis orthogonal to the first axis is set as a second axis; and
a display control unit configured to control a display unit to superimpose and display, on the fundus image, a display form representing the reference coordinate system.

9. The apparatus according to claim 8, further comprising:
an eye-to-be-examined information obtaining unit configured to obtain information about past tomographic imaging of the eye to be examined; and
a selection unit configured to select one of a preset apparatus coordinate system and the reference coordinate system based on the information,
wherein in a case where the selection unit selects the apparatus coordinate system, the obtaining position determination unit determines a tomographic image obtaining position based on the apparatus coordinate system.

10. An image processing apparatus comprising:
a fundus image obtaining unit configured to obtain a fundus image of an eye to be examined; and
an obtaining position determination unit configured to determine an obtaining position where a position crossing a line passing through a first position and a second position of the fundus image is obtained as a tomographic image of the eye to be examined containing a fundus position of the eye to be examined that corresponds to the first position.

11. The apparatus according to claim 10, further comprising:
- an extraction unit configured to extract a lamina cribrosa from the tomographic image obtained at the obtaining position; and
- a display control unit configured to control a display unit to display, together with the tomographic image, a display form representing a shape of the extracted lamina cribrosa.

12. An ophthalmologic apparatus comprising:
- a fundus image obtaining unit configured to obtain a fundus image of an eye to be examined;
- a detection unit configured to detect a position of an optic papilla region and a position of macular region of the eye to be examined from the fundus image;
- an obtaining position determination unit configured to determine, as an obtaining position where a tomographic image of the optic papilla region of the eye to be examined is obtained, a position crossing a line passing through the position of the optic papilla region and the position of the macular region; and
- a tomographic image obtaining unit configured to obtain the tomographic image of the optic papilla region at the obtaining position.

13. The apparatus according to claim 12, further comprising:
- an extraction unit configured to extract a lamina cribrosa from a tomographic image obtained at the obtaining position; and
- a display control unit configured to control a display unit to display, together with the tomographic image, a display form representing a shape of the extracted lamina cribrosa.

14. An ophthalmologic system comprising an image processing apparatus and an ophthalmologic apparatus,
the image processing apparatus including:
- a fundus image obtaining unit configured to obtain a fundus image of an eye to be examined;
- a detection unit configured to detect a position of an optic papilla region and a position of macular region of the eye to be examined from the fundus image; and
- an obtaining position determination unit configured to determine, as an obtaining position where a tomographic image of the optic papilla region of the eye to be examined is obtained, a position crossing a line passing through the position of the optic papilla region and the position of the macular region, and the ophthalmologic apparatus including a tomographic image obtaining unit configured to obtain the tomographic image of the optic papilla region at the obtaining position.

15. An image processing apparatus control method comprising:
- detecting a position of an optic papilla region and a position of macular region of an eye to be examined from a fundus image of the eye to be examined; and
- determining, as an obtaining position where a tomographic image of the optic papilla region of the eye to be examined is obtained, a position crossing a line passing through the position of the optic papilla region and the position of the macular region.

16. The method according to claim 15, further comprising:
- extracting a lamina cribrosa from the tomographic image obtained at the obtaining position; and
- controlling a display unit to display, together with the tomographic image, a display form representing a shape of the extracted lamina cribrosa.

17. A non-transitory computer-readable storage medium storing a computer program for causing a computer to execute each step of an image processing apparatus control method defined in claim 15.

18. An ophthalmologic apparatus control method comprising:
- obtaining a fundus image of an eye to be examined;
- detecting a position of an optic papilla region and a position of macular region of the eye to be examined from the fundus image;
- determining, as an obtaining position where a tomographic image of the optic papilla region of the eye to be examined is obtained, a position crossing a line passing through the position of the optic papilla region and the position of the macular region; and
- obtaining a tomographic image at the obtaining position.

19. A non-transitory computer-readable storage medium storing a computer program for causing a computer to execute each step of an ophthalmologic apparatus control method defined in claim 18.

20. An image processing apparatus control method comprising:
- obtaining a fundus image of an eye to be examined; and
- determining an obtaining position where a position crossing a line passing through a first position and a second position of the fundus image is obtained as a tomographic image of the eye to be examined containing a fundus position of the eye to be examined that corresponds to the first position.

21. A non-transitory computer-readable storage medium storing a computer program for causing a computer to execute each step of an image processing apparatus control method defined in claim 20.

* * * * *